US009211366B1

(12) United States Patent
Gutwein

(10) Patent No.: US 9,211,366 B1
(45) Date of Patent: Dec. 15, 2015

(54) NURSING MONITOR AND ASSOCIATED USE THEREOF

(76) Inventor: Jacob Gutwein, Monsey, NY (US)

( * ) Notice: Subject to any disclaimer, the term of this patent is extended or adjusted under 35 U.S.C. 154(b) by 324 days.

(21) Appl. No.: 13/589,013

(22) Filed: Aug. 17, 2012

Related U.S. Application Data

(60) Provisional application No. 61/524,503, filed on Aug. 17, 2011.

(51) Int. Cl.
A41C 3/04 (2006.01)
A61M 5/30 (2006.01)
A61M 1/06 (2006.01)
A61B 5/103 (2006.01)
A61B 5/00 (2006.01)

(52) U.S. Cl.
CPC .. *A61M 1/06* (2013.01); *A41C 3/04* (2013.01); *A61B 5/103* (2013.01); *A61B 5/4288* (2013.01); *A61B 5/4312* (2013.01); *A61B 5/6804* (2013.01)

(58) Field of Classification Search
CPC ........ A41C 3/04; A61B 5/4288; A61B 5/103; A61B 5/4312; A61B 5/3804; A61M 1/06
USPC ........ 600/587, 588, 58/9, 590, 591, 592, 593, 600/594, 595; 604/65, 66, 67, 74; 128/897, 128/898; 450/26, 36; 119/852, 14.12, 71
See application file for complete search history.

(56) References Cited

U.S. PATENT DOCUMENTS

| | | | |
|---|---|---|---|
| 6,478,739 B1 | 11/2002 | Hong | |
| 8,801,658 B2 * | 8/2014 | Harari et al. | 604/74 |
| 2003/0139662 A1 | 7/2003 | Seidman | |
| 2005/0020921 A1 | 1/2005 | Glassell et al. | |
| 2008/0077042 A1 * | 3/2008 | Feldkamp et al. | 600/547 |
| 2010/0217148 A1 * | 8/2010 | Binder | 600/547 |

* cited by examiner

*Primary Examiner* — Khoa Huynh
*Assistant Examiner* — Katharine Gracz

(57) ABSTRACT

A nursing bra for monitoring a child's milk intake during breast feeding procedures preferably includes a body adapted to be worn about a user breast, an electronic scale attached to the body for detecting a weight of the user breast, a monitor communicatively coupled to the electronic scale for receiving the weight of the user breast, a power source communicatively coupled to the scale and the monitor respectively. In this manner, the monitor displays a weight of the user breast before and after breast feeding procedures.

13 Claims, 4 Drawing Sheets

NURSING MONITOR AND ASSOCIATED USE THEREOF

CROSS REFERENCE TO RELATED APPLICATIONS

This application claims the benefit of U.S. Provisional Application No. 61/524,503 filed Aug. 17, 2011, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

1. Technical Field

This non-limiting exemplary embodiment(s) relates to breast feeding devices and, more particularly, to a nursing bra having an electronic scale to be worn over the breasts when nursing an infant in order to monitor a child's milk intake during breast feeding procedures.

2. Prior Art

Millions of women breast feed their babies. A natural means of transferring nutrients, nursing is beneficial to both the child and the mother. Encouraged by most pediatricians and medical associations, breast feeding during the first several months of life can provide a number of important advantages. Nursing is so important that a recent article published by the American Dietetic Association (ADA) strongly advocates and promotes breast feeding for its "indisputable nutritional, immunological, psychological and economic benefits." Some of the many benefits of breast feeding that have been documented include; fewer ear and respiratory infections, potentially fewer allergies, reduced incidence of blood infections, meningitis, cancer, insulin-dependent diabetes and most importantly, lower infant mortality rate and occurrences of Sudden Infant Death Syndrome (SIDS).

Additionally, breast milk transfers disease-preventing immunities from the mother to the child and is a recognized "brain food." For the nursing mother, benefits are also plentiful. In addition to creating a lasting bond between mother and child, women who nurse have lower occurrences of breast and ovarian cancer. Nursing triggers the uterine muscles, forcing them to constrict and return the uterus to the pre-pregnancy size and shape. Passing calories, fat and nutrients to their babies through the breast milk, mothers that nurse typically lose weight faster than those who do not. Furthermore, nursing one's child also saves potentially thousands of dollars in costly infant formulas and canned milk products.

While there is little dispute that nursing is both beneficial to the infant and mother, there is one drawback associated with breast feeding. Specifically, when nursing a child it can be difficult to ascertain exactly how much milk an infant has consumed. Should the infant not get enough milk, the result can be that they are left unsatisfied and irritable. Should the infant intake too much milk, the result can be a painful tummy ache, compromising the baby's well-being while also affecting their disposition.

Accordingly, a need remains for a nursing monitor in order to overcome shortcomings. The present disclosure satisfies such a need by providing a nursing bra having an electronic scale to be worn over the breasts when nursing an infant that is convenient and easy to use, lightweight yet durable in design, versatile in its applications, and designed for monitoring a child's milk intake during breast feeding procedures.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a nursing bra for monitoring a child's milk intake during breast feeding procedures. These and other objects, features, and advantages of the non-limiting exemplary embodiment(s) are provided by a nursing bra including a flexible body adapted to be worn about a user breast, an electronic scale attached to the body for detecting a weight of the user breast, a pull-cord channeled through the body wherein the pull-cord is selectively engaged with the electronic scale, and a controller attached to the body and communicatively coupled to the electronic scale for receiving the weight of the user breast. Advantageously, the controller calculates the milk intake from the weight of the user breast before and after breast feeding procedures.

In a non-limiting exemplary embodiment, the body has a circular shape and includes an outer edge continuously extending about an entire circular outer circumference of the body, an inner edge spaced from the outer edge wherein the inner edge continuously extends about an entire circular inner circumference of the body, an aperture formed within the inner edge, and sloped inner and outer surfaces each extending between the inner and outer edges. The inner and outer edges are non-planar.

In a non-limiting exemplary embodiment, the electronic scale is flexible and intercalated between the inner and outer surfaces.

In a non-limiting exemplary embodiment, the pull-cord includes opposed proximal and distal ends protruding out from the body. In this manner, the pull-cord is intercalated between the inner and outer surfaces and travels along a major arcuate path of the body defined between the inner and outer edges.

In a non-limiting exemplary embodiment, the pull-cord is disengaged from the electronic scale when the pull-cord is released to an equilibrium position along the arcuate path. Notably, the electronic scale has a first curvature when the pull-cord is at the released position.

In a non-limiting exemplary embodiment, the pull-cord is engaged with the electronic scale when the pull-cord is tightened to a tensioned position along the arcuate path. Notably, the electronic scale has a second curvature when the pull-cord is at the tensioned position.

In a non-limiting exemplary embodiment, the first curvature is less that the second curvature.

In a non-limiting exemplary embodiment, the body further includes a passageway directly abutted against the electronic scale and extends along the arcuate path. In this manner, the pull-cord is housed within the passageway.

In a non-limiting exemplary embodiment, the pull-cord is selectively reciprocated between opposed first and second walls of the passageway when the pull-cord is selectively pulled and released between the tensioned and equilibrium positions, respectively.

The disclosure further includes a method of utilizing a nursing bra for monitoring a child's milk intake during breast feeding procedures. Such a method includes the chronological steps of: providing a flexible body adapted to be worn about a user breast; providing and attaching an electronic scale to the body; providing and channeling a pull-cord through the body; providing and attaching a controller to the body; and communicatively coupling the controller to the electronic scale.

The method further includes the chronological steps of: the electronic scale detecting a weight of the user breast; the controller receiving the weight of the user breast; selectively engaging the pull-cord with the electronic scale as breast milk is consumed; and the controller calculating the milk intake from the weight of the user breast before and after breast feeding procedures.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
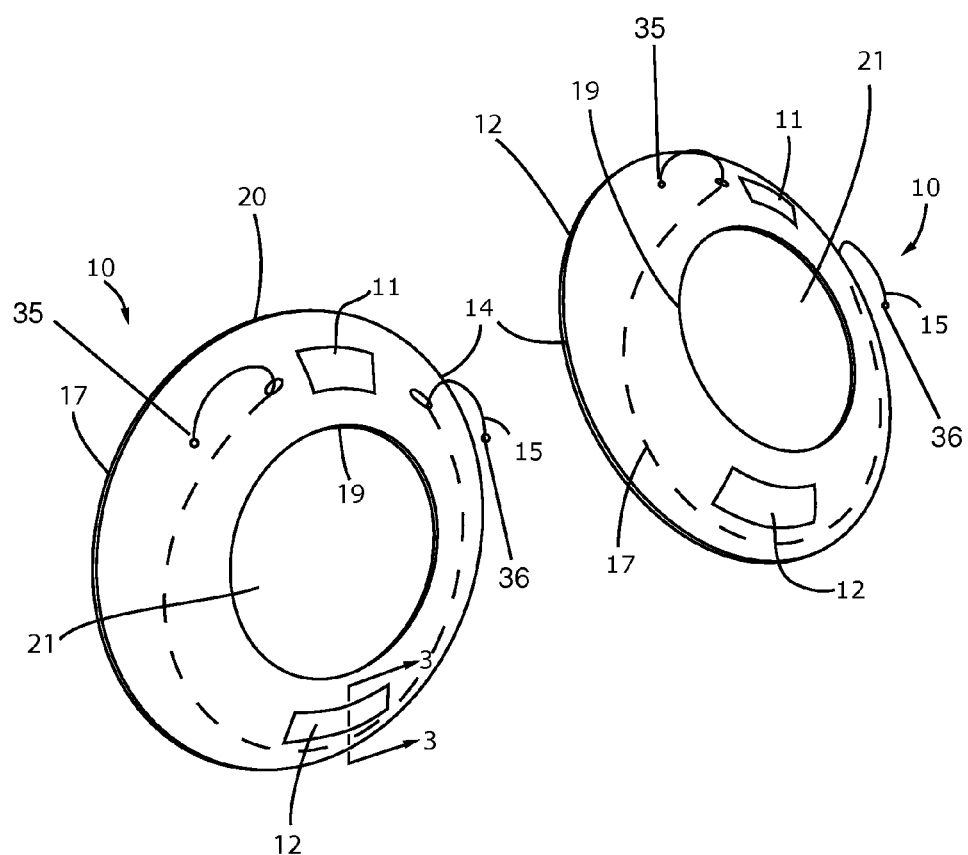
FIG. 1 is a perspective view showing a nursing monitor for measuring breast-milk consumption at an equilibrium position, in accordance with the non-limiting exemplary embodiment(s)

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-5 and is/are intended to provide a nursing bra with a built-in weight measuring device for detecting a quantity of milk consumed by an infant. It should be understood that such non-limiting exemplary embodiment(s) may be used to measure milk consumption from different types of female breasts, and should not be limited to the uses described herein.

Referring to the FIGS. 1-5 in general, a nursing bra 10 for monitoring a child's milk intake during breast feeding procedures is disclosed. The nursing bra 10 includes a flexible body 14 adapted to be worn about a user breast, an electronic scale 12 attached to the body 14 for detecting a weight of the user breast, a pull-cord 15 channeled through the body 14 wherein the pull-cord 15 is selectively engaged with the electronic scale 12, and a controller 11 attached to the body 14 and communicatively coupled to the electronic scale 12 for receiving the weight of the user breast. Advantageously, the controller 11 calculates the milk intake from the weight of the user breast before and after breast feeding procedures. For example, if the initial breast weight is three pounds and final breast weight is two pounds, than one pound of breast milk has been consumed. The controller 11 converts one pound of breast milk to a desirable unit such as ounces, cubic centimeters, etc.

In a non-limiting exemplary embodiment, the body 14 has a circular shape and includes an outer edge 20 continuously extending about an entire circular outer circumference of the body 14, an inner edge 19 spaced from the outer edge 20 wherein the inner edge 19 continuously extends about an entire circular inner circumference of the body 14, an aperture 21 formed within the inner edge 19, and sloped inner and outer surfaces 22, 23 each extending between the inner and outer edges 19, 20. The inner and outer edges 19, 20 are non-planar.

In a non-limiting exemplary embodiment, the electronic scale 12 is flexible and intercalated between the inner and outer surfaces 22, 23.

In a non-limiting exemplary embodiment, the pull-cord 15 includes opposed proximal and distal ends 35, 36, respectively, protruding out from the body 14. In this manner, a major longitudinal length of the pull-cord 15 is intercalated between the inner and outer surfaces 22, 23 and travels along a major arcuate path 17 of the body 14 defined between the inner and outer edges 19, 20.

Figure 3:
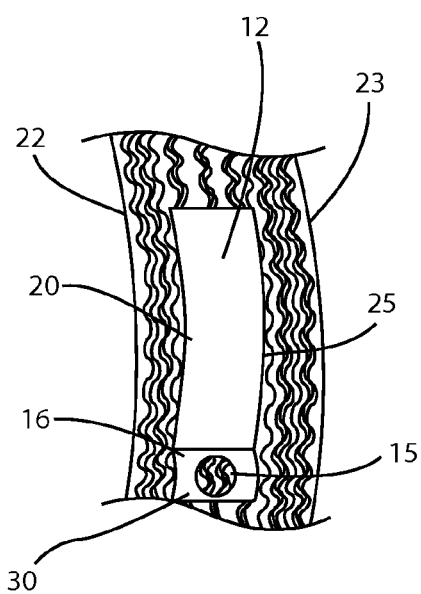
FIG. 3 is an enlarged cross-sectional view taken along line 3-3 in FIG. 1 wherein the pull-cord is released to the equilibrium position.

In a non-limiting exemplary embodiment, the pull-cord 15 is disengaged from the electronic scale 12 when the pull-cord 15 is released to an equilibrium position along the arcuate path 17 (FIGS. 1 and 3). Notably, the electronic scale 12 has a first curvature 25 when the pull-cord 15 is at the released position. Having the pull-cord 15 at the equilibrium position enables the caregiver to freely maneuver the breast through the aperture 21 as needed during breast insertion and removal procedures.

Figure 2:
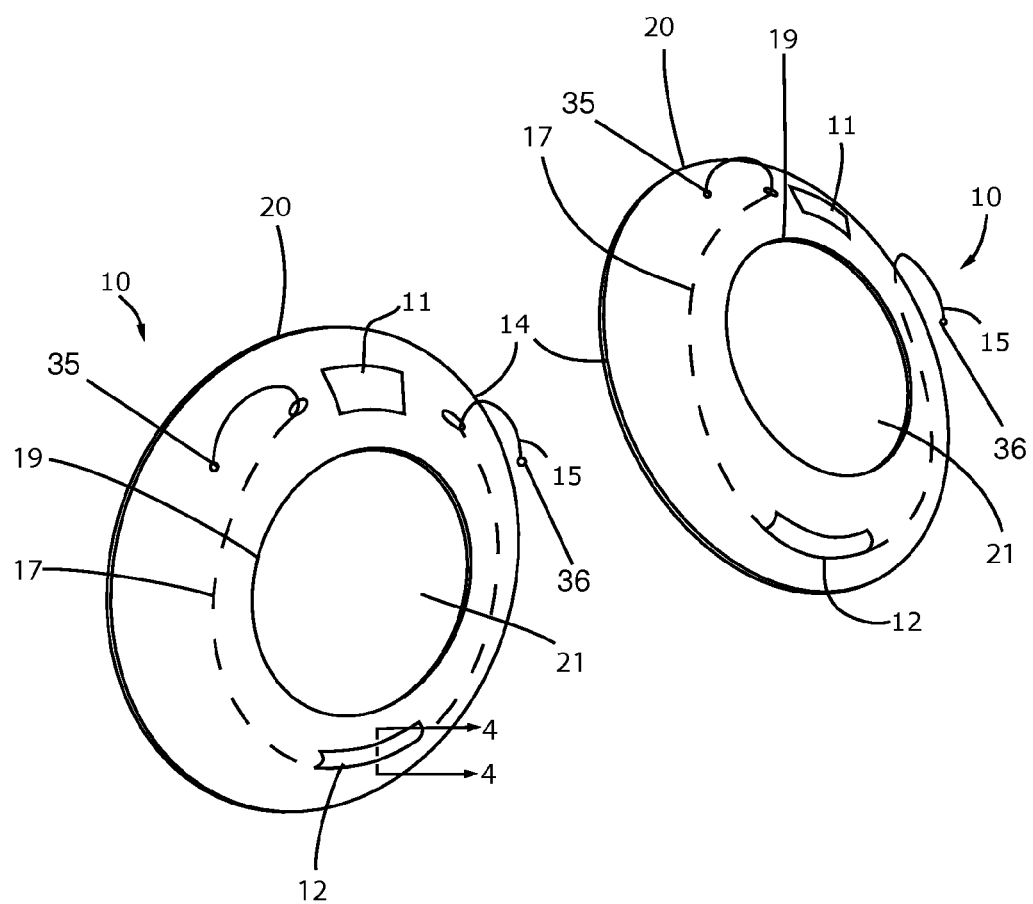
FIG. 2 is a cross-sectional view showing the nursing monitor of FIG. 1 at a tensioned position.
Figure 4:
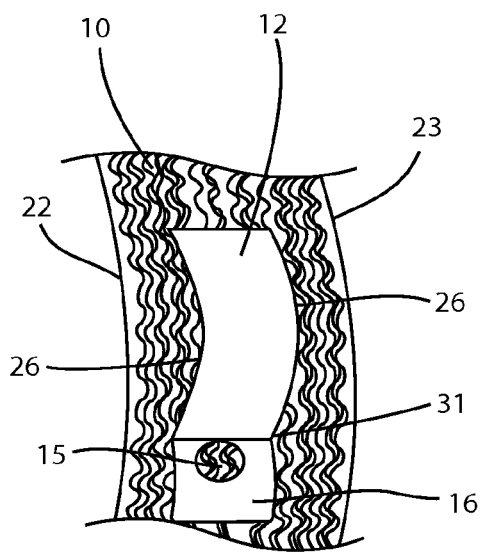
FIG. 4 is an enlarged cross-sectional view taken along line 4-4 in FIG. 2 wherein the pull-cord is pulled out to a tensioned position.
Figure 5:
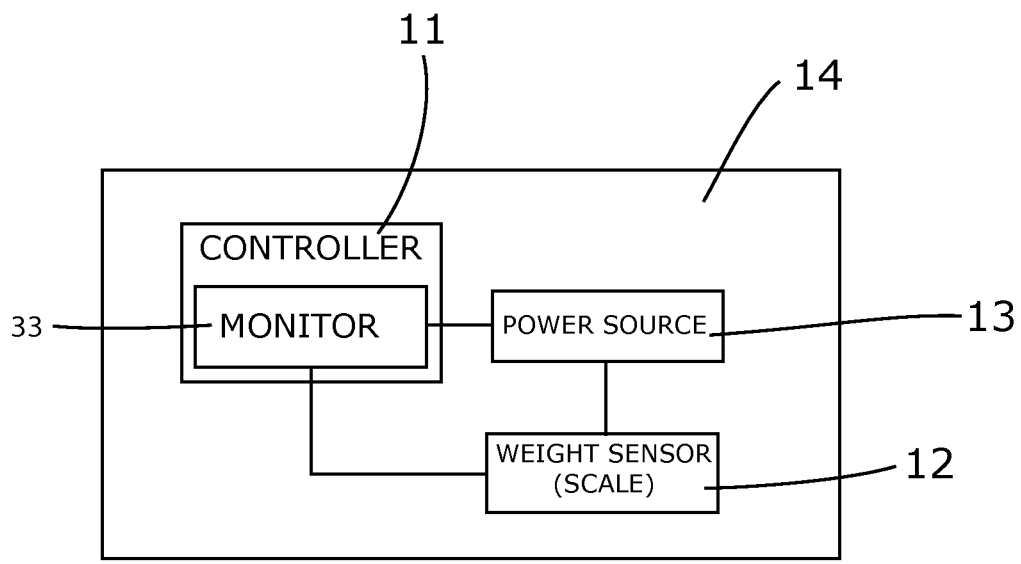
FIG. 5 is a schematic block diagram showing the interrelationship between the major electronic components of the present disclosure.

In a non-limiting exemplary embodiment, the pull-cord 15 is engaged with the electronic scale 12 when the pull-cord 15 is tightened to a tensioned position along the arcuate path 17 (FIGS. 2 and 4). Notably, the electronic scale 12 has a second curvature 26 when the pull-cord 15 is at the tensioned position. Having the pull-cord 15 at the tensioned position enables the caregiver to maintain continuous contact between the caregiver's breast and body 14 of the nursing bra 10 so that the electronic scale 12 accurately measures the breast weight as the size and shape of the breast change while discharging milk during feeding procedures.

In a non-limiting exemplary embodiment, the first curvature 25 is less that the second curvature 26.

In a non-limiting exemplary embodiment, the body 14 further includes a passageway 16 directly abutted against the electronic scale 12 and extends along the arcuate path 17. In this manner, the pull-cord 15 is housed within the passageway 16 and preventing from becoming unaligned with the electronic scale 12.

In a non-limiting exemplary embodiment, the pull-cord 15 is selectively reciprocated between opposed first and second walls 30, 31 of the passageway 16 when the pull-cord 15 is selectively pulled and released between the tensioned and equilibrium positions, respectively.

The disclosure further includes a method of utilizing a nursing bra 10 for monitoring a child's milk intake during breast feeding procedures. Such a method includes the chronological steps of: providing a flexible body 14 adapted to be worn about a user breast; providing and attaching an electronic scale 12 to the body 14; providing and channeling a pull-cord 15 through the body 14; providing and attaching a controller 11 to the body 14; and communicatively coupling the controller 11 to the electronic scale 12.

The method further includes the chronological steps of: the electronic scale 12 detecting a weight of the user breast; the controller 11 receiving the weight of the user breast; selectively engaging the pull-cord 15 with the electronic scale 12 as breast milk is consumed; and the controller 11 calculating the milk intake from the weight of the user breast before and after breast feeding procedures.

The nursing bra 10 is a cleverly designed device that enables nursing mothers to carefully and easily monitor their child's milk intake thereby determining how much milk a nursing infant has consumed while breast feeding. The nursing bra 10 may be configured in the form of a wearable bra, the cups of which may each feature integrated and sensitive electronic scales (sensors) 12 that measure the weight of the breasts. The body 14 of the bra 10 may feature apertures which enable the child to access the breast and nipple, without requiring the mother to remove the bra 10 from the breast.

In a non-limiting exemplary embodiment, adjustable shoulder straps, as well as a comfortable fastener may be positioned in the front or back of the bra 10 for added support.

In a non-limiting exemplary embodiment, the nursing bra 10 may feature integrated weight sensors 12 incorporated into the body 10. As such, the weight of the breasts prior to nursing the infant may be calculated and recorded via controller 11. The difference in the weight of the breast during and after the child has nursed determines how much milk the child has consumed. This information may be displayed on a monitor 33 or LCD panel removably attached to the controller 11, thus enabling the mother to carefully monitor the child as he or she consumed breast milk. The nursing bra 10 may be electronically powered and connected to any standard power outlet, or may run on internally contained batteries 13.

In a non-limiting exemplary embodiment, the body 14 may be formed as a wearable bra. The controller 11 may be communicatively coupled to a handheld diagnostic wand, which may screen for breast cancer and measure breast tissue density via ultrasound or Doppler technology.

In a non-limiting exemplary embodiment, the monitor 11 may include display screen configured for displaying various amounts of textual and/or graphical information. The display may be monochrome or color, of various physical dimensions, of various types. In one embodiment, the display may be suitable for displaying full motion video in color. By way of example and not limitation, the display may be comprised of a liquid crystal display (LCD); a field emission display FED; so called "E-ink" technologies, which employ microspheres having at least two reflectance states; a cathode-ray tube (CRT) display; a gas plasma display; an LED readout configured to display alpha-numeric and graphical information; or any other compatible visual display device. In a preferred implementation, the display is large enough to display, with clarity, one or more lines of information. Optionally, the display screen may be configured with a touch-screen interface, to present a user with a graphical user interface.

In a non-limiting exemplary embodiment, the power source 13 may include one or more rechargeable or non-rechargeable disposable batteries, photovoltaic cells, and/or an AC adapter or other power supply means.

The nursing bra 10 advantageously provides mothers who breast feed their infants a practical way to measure their child's milk intake. A cleverly designed measuring device configured in the form of a wearable body 14 and boasting integrated scales (sensors) 12 that weigh the breasts prior to, during and after nursing a child, enables the nursing mother to easily determine if her child has consumed enough milk to sustain them for the next several hours. With the nursing bra 10, the mother may easily monitor exactly how much breast milk their child has consumed, thus if the child has had too little may encourage them to eat more, or if the child has consumed the proper amount of milk for their size and age, pull them away from the breasts before they consume too much and develop a tummy ache or other discomfort. As such, this ensures a child was properly satiated and enjoys a peaceful night's rest or other scheduled activities, content and with a full belly.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A nursing bra for monitoring a child's milk intake during breast feeding procedures, said nursing bra comprising:
    a body adapted to be worn about a user breast;
    an electronic scale attached to said body for detecting a weight of the user breast;
    a pull-cord channeled through said body and selectively engaged with said electronic scale; said pull-cord comprises opposed proximal and distal ends protruding out from said body, said pull-cord being intercalated between inner and outer surfaces of said body and travels along a major arcuate path of said body defined between inner and outer edges of said body
    a controller communicatively coupled to said electronic scale for receiving the weight of the user breast;
    wherein said controller calculates the milk intake from the weight of the user breast before and after breast feeding procedures;
    wherein said body comprises a passageway directly abutted against said electronic scale and extending along said arcuate path, said pull-cord being housed within said passageway;
    wherein said pull-cord is selectively reciprocated between opposed first and second walls of said passageway when said pull-cord is selectively pulled and released between said tensioned and equilibrium positions, respectively;
    wherein when the body is in said tension position, said electronic scale engages said pull cord and allowing said scale to measure the weight of the user breast;
    and wherein when the body is in said equilibrium position, said electronic scale disengages said pull cord and is inoperative.

2. The nursing bra of claim 1, wherein said body has a circular shape and comprises:
    the outer edge continuously extending about an entire circular outer circumference of said body;
    the inner edge is spaced from said outer edge and continuously extending about an entire circular inner circumference of said body;
    an aperture formed within said inner edge; and
    sloped inner and outer surfaces each extending between said inner and outer edges; wherein said inner and outer edges are non-planar.

3. The nursing bra of claim 1, wherein said electronic scale is flexible and intercalated between said inner and outer surfaces.

4. The nursing bra of claim 1, wherein said pull-cord is disengaged from said electronic scale when said pull-cord is released to the equilibrium position along said arcuate path; wherein said electronic scale has a first curvature when said pull-cord is at said released position.

5. The nursing bra of claim 4, wherein said pull-cord is engaged with said electronic scale when said pull-cord is tightened to the tensioned position along said arcuate path; wherein said electronic scale has a second curvature when said pull-cord is at said tensioned position.

6. The nursing bra of claim 5, wherein said first curvature is less that said second curvature.

7. A nursing bra for monitoring a child's milk intake during breast feeding procedures, said nursing bra comprising:
    a flexible body adapted to be worn about a user breast;
    an electronic scale attached to said body for detecting a weight of the user breast;
    a pull-cord channeled through said body and selectively engaged with said electronic scale; said pull-cord comprises opposed proximal and distal ends protruding out from said body, said pull-cord being intercalated between inner and outer surfaces of said body and travels along a major arcuate path of said body defined between inner and outer edges of said body
    a controller fixedly attached onto said body and communicatively coupled to said electronic scale for receiving the weight of the user breast;
    wherein said controller calculates the milk intake from the weight of the user breast before and after breast feeding procedures;

wherein said body comprises a passageway directly abutted against said electronic scale and extending along said arcuate path, said pull-cord being housed within said passageway;

wherein said pull-cord is selectively reciprocated between opposed first and second walls of said passageway when said pull-cord is selectively pulled and released between said tensioned and equilibrium positions, respectively;

wherein when the body is in said tension position, said electronic scale engages said pull cord and allowing said scale to measure the weight of the user breast;

and wherein when the body is in said equilibrium position, said electronic scale disengages said pull cord and is inoperative.

8. The nursing bra of claim 7, wherein said body has a circular shape and comprises:
   the outer edge continuously extending about an entire circular outer circumference of said body;
   the inner edge is spaced from said outer edge and continuously extending about an entire circular inner circumference of said body;
   an aperture formed within said inner edge; and
   sloped inner and outer surfaces each extending between said inner and outer edges; wherein said inner and outer edges are non-planar.

9. The nursing bra of claim 8, wherein said electronic scale is flexible and intercalated between said inner and outer surfaces.

10. The nursing bra of claim 9, wherein said pull-cord is disengaged from said electronic scale when said pull-cord is released to the equilibrium position along said arcuate path; wherein said electronic scale has a first curvature when said pull-cord is at said released position.

11. The nursing bra of claim 10, wherein said pull-cord is engaged with said electronic scale when said pull-cord is tightened to the tensioned position along said arcuate path; wherein said electronic scale has a second curvature when said pull-cord is at said tensioned position.

12. The nursing bra of claim 11, wherein said first curvature is less that said second curvature.

13. A method of utilizing a nursing bra for monitoring a child's milk intake during breast feeding procedures, said method comprising the steps of:
   providing a flexible body adapted to be worn about a user breast;
   providing and attaching an electronic scale to said body;
   providing and channeling a pull-cord channeled through said body; said pull-cord comprises opposed proximal and distal ends protruding out from said body, said pull-cord being intercalated between inner and outer surfaces of said body and travels along a major arcuate path of said body defined between inner and outer edges of said body
   providing and attaching a controller to said body;
   communicatively coupling said controller to said electronic scale;
   said electronic scale detecting a weight of the user breast;
   said controller receiving the weight of the user breast;
   said body comprises a passageway directly abutted against said electronic scale and extending along said arcuate path, said pull-cord being housed within said passageway;
   said controller calculating the milk intake from the weight of the user breast before and after breast feeding procedures;
   selectively reciprocating said pull-cord between opposed first and second walls of said passageway when said pull-cord is selectively pulled and released between said tensioned and equilibrium positions, respectively;
   wherein when the body is in said tension position, said electronic scale engages said pull cord and allowing said scale to measure the weight of the user breast as breast milk is consumed;
   and wherein when the body is in said equilibrium position, said electronic scale disengages said pull cord and is inoperative.

* * * * *